United States Patent [19]

Witt

[11] 4,351,729

[45] Sep. 28, 1982

[54] BIOLOGICAL FILTER AND PROCESS

[75] Inventor: Enrique R. Witt, Corpus Christi, Tex.

[73] Assignee: Celanese Corporation, New York, N.Y.

[21] Appl. No.: 118,935

[22] Filed: Feb. 6, 1980

[51] Int. Cl.³ .............................................. C02F 3/28
[52] U.S. Cl. .................................... 210/603; 210/617; 210/631; 210/903
[58] Field of Search ....................... 210/603, 615–618, 210/631, 903

[56] References Cited

U.S. PATENT DOCUMENTS

| | | | |
|---|---|---|---|
| 3,520,802 | 7/1970 | Pavia | 210/631 |
| 3,709,364 | 1/1973 | Savage | 210/903 X |
| 3,846,289 | 11/1974 | Jeris et al. | 210/903 X |
| 3,867,284 | 2/1975 | Kappe et al. | 210/631 X |
| 4,043,936 | 8/1977 | Francis et al. | 210/903 X |
| 4,126,544 | 11/1978 | Baensch | 210/903 X |
| 4,182,675 | 1/1980 | Jeris | 210/903 X |
| 4,225,430 | 9/1980 | Bosman | 210/903 X |
| 4,256,573 | 3/1981 | Shimodaira et al. | 210/618 |
| 4,311,593 | 1/1982 | Benjes et al. | 210/603 |

FOREIGN PATENT DOCUMENTS 1462736 1/1977 United Kingdom .
1557282 12/1979 United Kingdom .

OTHER PUBLICATIONS

Lawrence et al., "The Role of Sulfide in Preventing Heavy Metal Toxicity in Anaerobic Treatment," *JWPCF* vol. 37, No. 3, pp. 392–405 (3/65).

*Primary Examiner*—Thomas G. Wyse
*Attorney, Agent, or Firm*—Stewart N. Rice; Ralph M. Pritchett

[57] ABSTRACT

A biological filter apparatus, and process for using the same, wherein organic pollutants in a waste water stream may be biologically degraded by a biomass of suitable microorganisms located on the surface of a packing. The filter comprises a sealed vessel in which the packing having the biomass thereon is located, and the waste water, mixed with several volumes of liquid recycle, is allowed to trickle downwardly through the packing countercurrently to ascending gases, effluent liquid is removed from the bottom of the vessel at a rate sufficient to maintain the level of effluent liquid below the packing in order to prevent the packing from being submerged in liquid. The apparatus and process are applicable to the anaerobic methanogenic processes wherein methane is produced as a product; and are also applicable to non-methanogenic processes which are conducted in the absence of added molecular oxygen wherein combined nitrogen is converted to molecular nitrogen. Extrinsic gases may be added to the filter at a point below the packing to aid in the degradation.

31 Claims, 1 Drawing Figure

U.S. Patent  Sep. 28, 1982  4,351,729
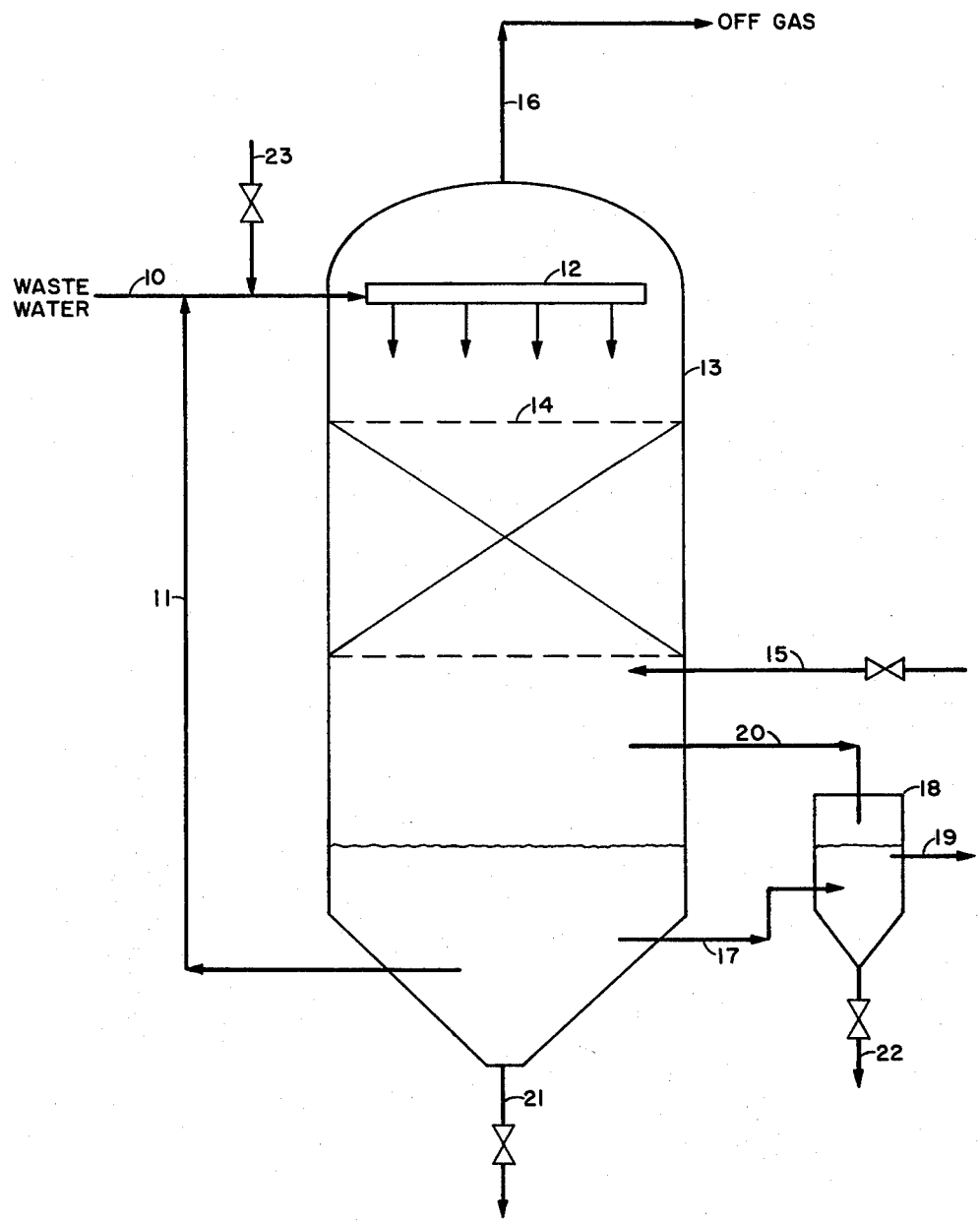

BIOLOGICAL FILTER AND PROCESS

BACKGROUND OF THE INVENTION

The disposal of many waste water streams presents environmental problems because of organic pollutants contained in the waste water. One method in which these waste water streams are treated in order to facilitate their disposal involves a biological degradation or conversion of the organic pollutants to nonoffending products and/or easily removable products. This is accomplished by contacting the stream with a biomass of microorganisms capable of biologically degrading or converting the pollutants to carbon dioxide and other products.

In an anaerobic, methanogenic process the microorganisms are anaerobic bacteria which convert the organic pollutants to mainly carbon dioxide and methane. The methane is valuable as an energy source. In some processes wherein not only degradation of organic pollutants occurs but denitrification is also accomplished, the organic pollutants are converted to carbon dioxide (no methane being produced) while combined nitrogen is converted to easily removable molecular nitrogen.

Various devices have been disclosed for conducting the biological degradation processes. One type of device is the lagoon which is merely a large pond or lake opened to the air. The waste water is placed in the lagoon and retained for several months, during which time both aerobic and anaerobic bacteria decompose the pollutants. The top layer of the lagoon will be aerobic in nature while the bottom will be anaerobic in nature. These lagoons are not suitable in most situations because of the large area needed, the odor produced, and their slow conversion time. Any methane produced is also, of course, lost entirely.

Another type of device in which biological degradation may be conducted in the absence of added molecular oxygen is a digester. A conventional digester is simply a closed vessel, with provisions for mild agitation and sized to provide at least 10 days detention time. The anaerobic digesters are practical only for high strength wastes such as thickened domestic sludge and certain food processing waste. They can be operated reasonably well when the feed contains solids, but they are relatively ineffective for effluents which contain only soluble pollutants.

The most popular device for treating waste water streams containing soluble organic pollutants is the device known as the anaerobic filter. It consists of a packed tower containing packing on which is disposed a biomass of suitable microorganisms. In those anaerobic filters heretofore disclosed, the effluent or waste water stream was passed upward under plug flow conditions through the packed section, fresh feed being passed to the bottom of the packed tower with liquid overflow being removed at a point above the packed section. Under such conditions of operation, the packed tower would be filled with liquid at all times with the liquid level in the tower being maintained above the upper end of the packed section. Because, under such conditions of operation, the tower will be filled with liquid at all times, the tower must be constructed of a heavy and strong material (such as steel) which is relatively expensive.

A device similar to the anaerobic filter is also known in prior art for conducting an aerobic biological degradation process. More specifically it has been disclosed that an aerobic biological degradation process may be conducted by distributing the process liquid over the top of an open, packed vessel containing packing on which is located aerobic microorganisms, and allowing the liquid to trickle downwardly through the packing and in contact with the aerobic microorganisms. Being open to the air, these packed vessels would not be suitable for processes which must be conducted in the absence of molecular oxygen. The aerobic processes are not as desirable as the anaerobic processes because no methane, a potential energy source, is produced, the main products being carbon dioxide and water.

The anaerobic filter device described above is very useful in the treatment of waste water streams which contain no appreciable amount of solids, that is those in which the pollutants are soluble. Even though extensive research and development work has been done on the anaerobic filter devices, various problems still exist with their use. The cost of constructing a filter vessel using the upward plug flow as practiced in the prior art is mentioned above. Another problem with the anaerobic filter devices, as utilized in the prior art, is that there is a tendency, particularly when the linear velocity of liquid through the filter is quite low, for the biomass in the lower, or inlet portion of the filter to become so lush in its growth habit as to clog the filter. Further, if the linear velocity of the waste water stream through the filter is too high, such can result in inhibition or destruction of the biomass because the concentration of the pollutants will be increased above the level which can be tolerated by the microorganisms.

It is an object of the present invention to provide a new and useful biological degradation process for the treatment of waste water streams, and a new and useful apparatus therefor. It is an additional object of the present invention to provide a new and useful methanogenic biological degradation process of the anaerobic filter-type, and apparatus therefor, which utilizes relatively lightweight and inexpensive materials of construction. It is a still further object of the present invention to provide a new and useful anaerobic filter process and apparatus wherein the distribution of the process liquid through the filter is relatively simple, and which will readily free itself from accumulated biomass or other solids. Another object of the present invention is to provide an anaerobic filter process and apparatus which, unlike the prior-art anaerobic filter processes and apparatus, will handle and degrade some types of solid pollutants. Additional objects will become apparent from the following description of the invention.

SUMMARY OF THE INVENTION

The foregoing and additional objects are accomplished by the present invention which in one of its aspects is a continuous biological degradation process wherein a liquid waste water stream containing organic pollutants amenable to biological degradation is contacted with a biomass of microorganisms located on the surface of a support packing so as to effect the biological degradation of said organic pollutants to carbon dioxide and other products, said microorganisms being capable of degrading said organic pollutants to carbon dioxide and other products, said process being conducted in the absence of added molecular oxygen, which process comprises:

(a) continuously passing a liquid mixture comprised of said waste water stream and the hereafter defined recycle stream downwardly through a packed section confined within a sealed vessel, said packed section being filled with the said support packing on the surface of which is a said biomass of said microorganisms, said sealed vessel being sealed whereby air and other sources of molecular oxygen cannot enter said sealed vessel, such that said liquid mixture intimately contacts said biomass as it descends through said packed section under conditions whereby at least a portion of the organic pollutants from said waste water stream are biologically degraded and converted to carbon dioxide and other products and resulting in a liquid effluent from the lower end of said packed section containing a lower concentration of said organic pollutants than in said liquid mixture, and whereby liquid descends through said packed section while carbon dioxide and other gases generated in the biological degradation ascend through said packed section countercurrently to the descending liquid, the contacting of said liquid mixture with said biomass being accomplished at a temperature within the range of about 10° to 60° C. which is suitable for said biological degradation and at substantially atmospheric pressure;

(b) continuously withdrawing from the upper end of said sealed vessel at a point above said packed section the said carbon dioxide and other gases generated in the said biological degradation;

(c) continuously withdrawing said liquid effluent from the lower end of said sealed vessel at a point below said packed section, the rate of withdrawal of said liquid effluent being such as to maintain the liquid level of any said liquid effluent accumulating in the bottom of said sealed vessel below said packed section, a portion of said liquid effluent being withdrawn as a treated waste water outfall stream; and (d) continuously recycling as a said recycle stream a portion of said liquid effluent withdrawn from the lower end of said sealed vessel and mixing said recycle stream with said waste water stream prior to passing the resulting said liquid mixture downwardly through said packed section in accordance with the preceding step (a), the portion of said liquid effluent so recycled as said recycle stream being an amount that, when mixed with said waste water stream, will cause the said liquid mixture to have a concentration of said organic pollutants and of any biostatic or biocidal species to be below that concentration which would inhibit the growth processes of said microorganisms.

In another aspect, the present invention is a biological filter apparatus for effecting the foregoing biological degradation process.

BRIEF DESCRIPTION OF THE FIGURE

The FIGURE is a flow diagram of a biological filter operated in accordance with the present invention.

DETAILED DESCRIPTION OF THE INVENTION

The main differences between the filter of the present invention, and its operation, are that the liquid is passed downwardly through the packing countercurrently to gases which are ascending within the packing, and that the packing is gas-filled instead of being submerged or liquid filled. These differences alleviate many problems associated with the prior art filters. Thus, the filter of the present invention presents an improvement in that it, not being liquid filled, may be contained in a much lighter and less expensive structure. Another improvement represented by the filter of the present invention is that feed distribution is very simple, a sprinkler being sufficient. Further, unlike prior art upflow anaerobic filters, the filter of the present invention can readily free itself of accumulated biomass or other solids. The filter of the present invention can also degrade some types of solids without the necessity of their being dissolved or solubilized. The filter of the present invention also allows the contact of the waste water with external gases in situations where such is desirable. These improvements will be more fully explained in the succeeding paragraphs.

Reference is made to the figure which illustrates an operation of a filter in accordance with the present invention. Waste water to be treated introduced through line 10 is mixed with a liquid recycle stream from line 11 and then passed to a sprinkler device 21 located in the upper end of a sealed, packed tower 13 containing packed section 14. Located on the surface of the packing in the packed section is a suitable biomass of organisms. The liquid mixture of fresh waste water and recycle liquid is sprayed or sprinkled onto the packing contained in the packed section 14 and allowed to trickle downwardly through the packing.

Ascending in the packing countercurrently to the descending liquid are gases generated in the biodegradation such as carbon dioxide, and in a methanogenic process, methane. External gases may also be introduced at a point below the packed section through line 15 and these external gases will also ascend through the packed section. Gases which eventually ascent to the upper end of packed tower 13 are removed as off gas through line 16.

Liquid which has descended through the packing accumulates in the conical bottom section of tower 13. The level of this liquid is controlled by conventional means so as to always be below the packed section in order that the packed section be gas filled and not submerged in liquid. A large portion of the accumulated liquid is recycled through line 11 while a liquid product of improved purity is removed through line 17. This liquid product removed through line 17 has a lower content of pollutants than the waste water. As indicated in the FIGURE, it is generally desirable to pass the liquid product removed through line 17 to a settler 18 where suspended solids are allowed to settle out, treated liquid product being ultimately withdrawn from settler 18 through line 19. A line 20 connects the gas phase of tower 13 and settler 18 so they are in hydraulic balance. The liquid product removed through line 19 is generally termed as the "outfall" and will hereafter be referred to as such. The outfall may be further treated for removal of other impurities; and, in one preferred form, the outfall is fed to an aerobic digester for removal of a substantial percentage of its remaining content of dissolved biodegradable material or for the oxidation of foul smelling components such as hydrogen sulfide. In an anaerobic digestion this dissolved biodegradable material is used to support the growth of bacteria, so that it is converted into the solid form (comprising a mass of bacteria) known as "activated sludge".

In one preferred form of the invention, a significant portion of this activated sludge is recycled to the filter, for example, through line 23. It has been found that the activated sludge is at least partially converted in the filter. This reduces the amount of solids formed in the overall process. The portion of the activated sludge which is degraded appears to be the soluble portion which is solubilized in the aqueous medium prior to degradation; however, in some instances the anaerobic filters of the present invention will degrade some types of solid pollutants without them first being dissolved or solubilized. More specifically the present invention will, for example, biologically degrade water insoluble starch, and this is totally unexpected.

The bottom of tower 13 is fitted with valve 21 which may be periodically opened to allow removal of accumulated biomass which has been torn or otherwise displaced from the packing, as well as to allow removal of other solids which may accumulate. One advantage to the liquid downflow of the present invention is that biomass which comes free from the packing will eventually work its way naturally and by gravity downwardly through the packing to the reservoir at the bottom of the tower where it is easily removed. This prevents the blinding or clogging frequently caused by loose biomass in an upflow filter. Settler 18 is also fitted with a valve 22 to allow removal of accumulated solids. Biological solids removed from the bottom of tower 13 and to the bottom of settler 18 may be returned, if desired, to the filter.

Even though in operation according to the present invention some flaking or detachment of biomass occurs, the attachment of biomass to the packing is quite firm. The attachment of the biomass appears to be much firmer than the biomass of the submerged upflow filters of the prior art. While the biomass of prior art submerged filters is loosely attached and easily washed off by mild hydraulic action, the biomass of a filter of the present invention resists the scouring effect of liquids percolating through the packing surprisingly well, and much better than that of the submerged filters.

The packing in the filter (the filter being the packed section) is preferably such as to provide a void volume (volume of empty unpacked filter minus volume actually occupied by the solid of the packing) well above 60%, more preferably above 75% such as 85 to 95% or more, of the volume of the unpacked filter, that is the unpacked volume of the packed section. This can be accomplished with thin-walled plastic rings or cylinders, such as the packing known as Pall rings which are described in Chemical Engineering Process 54 (1), 1958, pages 70–75. The ring diameters may be, for instance, in the range of about $\frac{5}{8}''$ to 4", and are preferably at least about 3 inches for use in a large scale anaerobic filter. Other types of packings providing high void volumes and preferably high surface areas (e.g. surface areas of well over 10 sq. ft. per cubic foot of packing, preferably above 20, such as about 30 sq. ft. per cubic or more) may be used, such as apertured plastic saddles, or cylindrical brushes comprising tufts of plastic bristles symmetrically arranged around a stainless steel wire core. Aluminum beverage cans could also be used. The loading on the filter in our process is generally from about 0.2 to 4.0, and preferably from about 0.5 to 2.0, lb. C.O.D. per cubic foot of void volume of the filter per day, e.g. a loading of 1 or even 2 lb. C.O.D. per cubic foot of void volume per day. The term "C.O.D." as used herein and in the claims refers to the chemical oxygen demand as determined by standard methods. The hydraulic feed rates will generally be such that volume of total fresh liquid feed and recycled liquid material will be from about 0.1 to 10 times the void volume of the filter per day.

In one preferred practice of the invention the fresh waste water feed has a C.O.D. of above 2000, usually above 5000 or 6000 mg/l (milligrams per liter). The process is particularly suitable for fresh feeds having C.O.D. values above 10,000, such as 20,000 to 40,000 mg/l or even 50,000 mg/l or more. The total blend of fresh waste water feed and recycled material fed to and passed downwardly through the filter generally will have a C.O.D. in the range of about 500 to 20,000 mg/l, preferably about 1000 mg/l or more.

In the operation of the filters it has been found that the amount of biomass adhering to the packing, even after extended operation, is such as to occupy only a small fraction of the void volume (this being measured by allowing the contents of the filter to drain out and measuring the volume of the liquid thus removed), even though there is a significant recycle of biomass to the filter. While the reasons for this are not clearly understood, it is believed that the recycled bacteria serve, in part, as food for the bacteria in the filter. It is also found, on inspection of filters after lengthy (e.g. 6 months or more) operation under recycle that the biomass attached to the filter packing is distributed on the packing substantially throughout the filter. Visually this distribution of biomass appears to be substantially uniform from top to bottom.

The content of biomass in the outfall of the anaerobic filter (operated with recycle of effluent and of settled particles of biomass therein) is quite low, such as less than 600, e.g. about 100 to 500, such as about 300 mg VSS (volatile suspended solids) per liter.

The aqueous waste streams which may be treated in accordance with this invention include those from petrochemical plants, which may contain, for example, acids (e.g. such carboxylic acids as formic, acetic, propionic, acrylic, glycollic, maleic, adipic, benzoic, butyric, valeric, hydracrylic, glyceric, succinic, fumaric, glutaric, phthalic, isophthalic, terephthalic); alcohols (e.g. methanol, ethanol, n-propanol, ethylene glycol, polyethylene glycol, 1-butanol, 2-butanol, iso-butanol, propylene glycol, 1,3-butyleneglycol, 1,5-pentanediol, 1,6-hexanediol, glycerol); ketones (e.g. acetone, methyl ethyl ketone, cyclohexanone); esters (e.g. such carboxylic esters as ethyl acrylate, methyl propionate, methyl hydrogen adipate, methyl methacrylate); aldehydes (e.g. formaldehyde, acetaldehyde, acrolein, methacrolein, glyceraldehyde, benzaldehyde); phenols (e.g. phenol or cresol). The materials may be aliphatic, cycloaliphatic or aromatic, and ethylenically saturated or unsaturated. It is found that compounds which are ordinarily considered to be highly biocidal such as formaldehyde, phenol and acrolein and cyanide ion can be removed even when present at relatively high levels in the feed stream. For instance the feed stream may contain over 1000 mg/l of formaldehyde (such as 0.1 to 1%) or 2000 mg/l of phenol. In general the ingredients of a waste stream from a petrochemical plant will have less than 9 carbon atoms, preferably below 7 carbon atoms; often they will be largely organic compounds having 1 to 4, or even 1 to 2, carbon atoms.

In addition to treating waste streams from petrochemical plants, various other waste streams may be treated in accordance with the invention. For example waste water streams arise in the food industry which contain polysaccharides, such as starch and guar, proteins and fats. These polysaccharides may be deploymerized in accordance with the invention and many of the proteins and fats can also be decomposed according to the invention. Even granular, insoluble starches, such as potato starch, will be extensively biodegraded according to the present invention. This is entirely unexpected since the prior art has generally been of the opinion that starches would be broken down by enzymes only after being gelatinized. Fats yield very little energy on dismutation to methane and carbon dioxide and do not biograde very extensively; however the filters of the present invention perform much better than the submerged filters of the prior art because the filters of the present invention free themselves of particulate solids much better than the submerged filters. Proteinaceous materials, excepting perhaps lipids, should also be biodegraded well according to the invention.

In an anaerobic methanogenic process, certain components, even in relatively small amounts, will be generally incompatible with the operation of the anaerobic filter and their presence in interfering amounts should therefore be avoided; these include the chlorinated methanes, e.g. methylene chloride, chloroform, carbon tetrachloride and precursors thereof such as chloral, and certain amines such as hexamethylenediamine. The chlorinated methanes, the amines, etc. do not however appear to be toxic to a filter operated according to the invention wherein denitrification is being accomplished. Certain other compounds are not incompatible with the operation of the filter but pass through it largely unaffected; among these are highly branched compounds such as pentaerythritol, neopentyl glycol, trimethylolpropane and t-butanol (e.g. compounds in which there are tertiary carbons to which most of the carbons are directly attached) and non-hydrolyzable polymers such as polyacrylic acid. These compatible non-degrading components may be present in the waste streams treated in accordance with this invention; and their presence increases the measured C.O.D. level but does not represent an actual load on the filter and the C.O.D. loads given herein have been corrected, when necessary, to exclude the contribution to C.O.D. of such non-degradable materials, when present.

Some feed streams will contain otherwise toxic heavy metals, such as copper, nickel, chromium, zinc, mercury or nickel. In that case it will be desirable to provide a sufficient amount of sulfur to the feed (e.g. in the form of soluble sulfide or sulfate such as sodium sulfate) to combine with the heavy metal and precipitate it as the insoluble sulfide. See Lawrence and McCarty "The Role of Sulfide in Preventing Heavy Metal Toxicity in Anaerobic Treatment" J. Water Pollution Control Federation 37 (1965 p. 392–406). Chromium, which does not form an insoluble sulfide, is probably immobilized as a basic oxide. The sulfur may also be conveniently added in the form of hydrogen sulfide gas at a point below the filter, as through line 15 of the figure, so as to ascend through the filter countercurrently to the descending liquid. This will provide intimate contact between the descending liquid and the ascending hydrogen sulfide.

As mentioned, the present invention is applicable not only to an anaerobic methanogenic process, but is also applicable to the processing of waste water streams which contain, in addition to the organic pollutants described above, combined nitrogen present as the nitrogen in a nitrogen oxide, a nitro radical, a nitroso radical, a nitrite radical or a nitrate radical. These type waste water streams are treated so as to biologically degrade the organic pollutants to mainly carbon dioxide and to convert or degrade combined nitrogen present as nitrate, etc. to molecular nitrogen, there being no methane produced in such processes. These processes wherein denitrification is additionally accomplished are conducted in the absence of any external or added molecular oxygen although they are not, perhaps, truly anaerobic in nature since some oxygen radicals are produced in the conversion of the combined nitrogen to molecular nitrogen. The oxygen so produced does not become molecular oxygen and instead oxidizes any organics to carbon dioxide. For example, nitric acid would be converted to molecular nitrogen according to the following reaction:

$$2HNO_3 \rightarrow H_2O + N_2 + 5[O] \qquad \text{I}$$

The five oxygen radicals so produced would oxidize the organics present to carbon dioxide. Thus, in a denitrification process the main function is to clean a waste water stream of obnoxious pollutants, with no useful methane being produced.

In this denitrification, any of the nitrogen oxides, such as $N_2O$, $NO_2$ and $NO$ will be converted to molecular nitrogen and oxygen radicals. Nitrates which may be converted include nitric acid, nitroglycerin, uranyl nitrate, ammonium nitrate, sodium nitrate, potassium nitrate, calcium nitrate and the like. These nitrates could, for example, be those nitrates typically found in the effluent or runoff from explosives manufacture, agricultural processing and uranium processing. Nitrates such as pentaerythritol tetranitrate would probably be hydrolyzed and then degraded in the process. Nitrites which may be converted include sodium nitrite, potassium nitrite and the like. The range and type of nitrites likely to be encountered in a process effluent are fewer than the nitrates.

Practically any organic compound containing a radical having combined nitrogen and oxygen (nitro, nitroso, nitrate and nitrite) can be treated according to the invention, although the nitrates, etc. which may be treated are not limited to organic nitrates as may seem from the foregoing. The invention will of course perform better and provide more degradation on some organic nitrogen compounds than others. Nitromethane is a particular organic nitrogen compound which will be substantially totally degraded.

The process and apparatus of the particular invention is better suited for a denitrification than the submerged filters of the prior art in that intermediate nitrogen oxides formed in the denitrification have a chance to redissolve in the liquor and be further converted to molecular nitrogen; whereas, bubbles containing nitrogen oxides which are formed in the submerged filter devices can easily escape the system without allowing the nitrogen oxide intermediates to redissolve and react. This is particularly true where the waste water stream contains combined nitrogen in the nitrate form wherein $N_2O$ is formed as an intermediate. Of course, in a denitrification, the various advantages mentioned above as to lightweight construction, easy removal of detached biomass, etc. are also applicable.

In a denitrification process conducted in accordance with the present invention, additional oxidation of organic pollutants could be accomplished by introducing nitrogen oxides, particularly $N_2O$, to the filter at a point below the packing, as for example through line 15 of the figure. The $N_2O$ thus introduced would ascend through the packing and act as a biological oxidizer, the $N_2O$ being converted to molecular nitrogen and to oxygen radicals, which oxygen radicals would serve to oxidize organic pollutants present in the waste water. Frequently, N₂O is present in large amounts in a processing plant as an off gas and the present invention would allow its use as a biological oxidizer.

In an anaerobic methanogenic process wherein denitrification is not being accomplished, it will be advantageous to feed hydrogen to the filter at a point below the packing. The hydrogen will react with carbon dioxide to form methane according to the following reaction:

$$CO_2 + 4H_2 \rightarrow CH_4 + 2H_2O \qquad \text{II}$$

This is of interest for a location where excess hydrogen is available. By such use of hydrogen, the off gas removed from the filter would be enriched in methane, increasing its fuel value. Also the carbon dioxide content of the off gas would be reduced, which would result in a reduced concentration of dissolved carbon dioxide, and this should allow operation with less alkalinity in the feed. Addition of hydrogen should be less than stoichiometric relative to carbon dioxide produced in the filter so that at least small amounts of carbon dioxide remain in the offgas.

In the startup of a process operated in accordance with the present invention, a suitable biomass of microorganisms for the digestion of the particular waste water stream will normally be "cultivated" in-situ by initially feeding the filter with a microorganism sludge initially obtained from, for example, the soil or process drain lines in the immediate vicinity, and then allowing growth and evolutionary development of this initial inoculum into a biomass which will be inherently adapted to metabolic conversion of the substrate (that is the waste water stream) in which the inoculum has been developed. The biomass forms more slowly, in general, than the biomass of a submerged filter and this may be due to the fact that the filters of the present invention require the development of a more "sticky" or adhesive flora than required in the submerged filters. The more adhesive flora is needed so as to resist the hydraulic action of the liquid as it trickles downwardly through the packing. Because of the fact that the biomass developed in a submerged filter is rather loosely attached to the packing, such a filter could not be switched to operation according to the present invention without a long break-in period to develop a more adhesive flora. The biomass coated packing of a submerged filter would be stripped of biomass relatively quickly if subjected to the trickle flow of the filters of the present invention.

In an anaerobic methanogenic process, the decomposition of organic pollutants takes place in two basic stages utilizing two different types of microorganisms. One set of microorganisms is generally referred to as the "acid formers" and the other set as the "methane formers". The organic pollutant is first converted to carboxylate moieties by the acid forming microorganisms, and then these carboxylate moieties are further converted to methane and carbon dioxide by the methane forming microorganisms. In the submerged, plug-flow filters of the prior art, the first stage biomass is generally located at the inlet or lower end of the filter while the second stage biomass is located at the outlet or upper end of the filter. In the trickle filter of the present invention, the first stage microorganisms and the second stage microorganisms do not appear to be located in separate areas of the filter, and both stages appear to be uniformly distributed throughout the filter.

In an anaerobic methanogenic process, the second stage, or methane forming, microorganisms are normally much more sensitive to environmental changes than are the acid forming species found in the first stage, and they are much more sensitive to pH in particular. Their rate of growth is less rapid than that of the acid forming organisms, and they regenerate themselves much more slowly after being damaged than do the acid formers.

In a process conducted according to the present invention where denitrification is also accomplished, experiments indicate that only one set of microorganisms is present. This should not, however, be taken as a limitation on the present invention since there might be two or more types of microorganisms involved. For example one type of microorganism might convert large organic molecules while another type converts smaller organic molecules. The microorganisms in these processes are less sensitive to environmental changes, and in particular are less sensitive to pH, than those of the anaerobic methanogenic processes.

In operating according to the present invention, it is necessary that a large portion of the liquid effluent which descends from the packing and which accumulates in the bottom of the tower be recycled and mixed with fresh waste water. This recycle is mainly for two purposes. First, a high recycle rate is necessary so that the liquid mixture passed to the filter does not contain contaminants in a concentration which is above the level at which they inhibit the life processes of the microorganisms in the filter. This avoids destruction or inhibition of the biological process occurring within the filter. Second, in many cases it also eliminates, or substantially reduces, the need for employing alkaline reagents to adjust the pH of the waste water prior to treatment because the effluent of the filter commonly contains alkaline bicarbonates produced in the treatment process. The exact amount recycled will vary from process to process but it can generally be stated that at least 60%, and preferably at least 90%, of the liquid effluent accumulating in the bottom of the packed tower be recycled and mixed with fresh waste water feed before being again passed through the filter. The ratio of recycled liquid effluent (line 11) to fresh waste water feed (line 10) (weight ratio) will generally be within the range of about 5:1 to 100:1, more usually within the range of about 8:1 to 25:1. The ratio of liquid effluent recycled to fresh waste water will be very slightly lower than the ratio of effluent recycled (as through line 11) to effluent taken as product (as through line 17) because of the conversion of liquid to gas in the filter.

The optimum recycle rate will vary from process to process and waste water stream to waste water stream, the fundamental controlling factor being the concentration of pollutants in the waste water stream which is to be treated. Since there is wide variation among the many species of microorganisms used in biological digestions, and since there is also an extremely wide variation in composition of the infinitely large number of waste streams which it may be desired to subject to biological digestion, it is not possible to present meaningful quantitative data for the maximum allowable pollutant concentration of all potential waste streams with all potential biomasses which may be found in biological treatment systems (each biomass being the result of individual evolutionary adaptation to the particular environment). Also a given waste stream may contain a high loading of comparatively innocuous substrates which could be successfully digested in high concentration but for the presence of a very minor portion of some particularly difficult chemical species, such as formaldehyde, phenols, acrolein, chloroform, or various mercury compounds. Typically, however, organic compounds which have no pronounced biocidal or biostatic action in substantially neutral aqueous solutions (e.g., solutions having a pH of about 6.0 to 8.0 for an anaerobic methanogenic process and about 6.0 to 9.0 for a denitrification process) do not inhibit the metabolic processes of the microorganisms used in these digestions if their concentration in the liquid passing through the biomass is no greater than that at which the chemical oxygen demand (C.O.D.) of the liquid is about 2000 mg of oxygen per liter. This figure is offered by way of general guidance, rather than as a limitation of the present invention, inasmuch as it will be understood that some materials, such as sugars, are extremely susceptible to biological digestion even at "syrup" concentrations while others, especially when they contain trace quantities of biocides or biostats, are much less so. In the latter case a very small quantity of a strong biocide or biostat can be the determining factor affecting maximum allowable substrate loading.

With further reference to the foregoing, it will be understood that waste streams are frequently encountered in which there is a biostatic or biocidal effect due to the presence of inorganic contaminants, with the organic materials which are present being quite innocuous to the biomass and not a controlling factor. Heavy metals, for example, present a problem of this sort. In these cases it will be understood that, if it is not feasible to remove these inorganic materials, as by chemical methods, before the biological treatment, then the limiting factor in determining the minimum dilution ratio to be employed with such materials in the present improved treatment process is the maximum allowable concentration of these inorganic species, rather than that of the organic components in the waste stream being treated. As explained above, properly controlled biological digestion can actually result in abstraction of heavy metals from the waste water by the biomass through the addition of sulfur compounds.

In determining the maximum allowable concentration of pollutant species in the diluted liquid which is to be passed through the digester or filter, there will be, of course, some instances in which it is known from the prior art what level of substrate can be tolerated without affecting the biomass adversely. In other instances, however, as when the waste water to be processed is one which is new to the art, the most practical approach is to actually study the behavior of the new substrate in the laboratory by standard experimental biological techniques. That is, a laboratory-size digester is seeded with a suitable inoculum which is then acclimated with continuously-increasing concentration of the pollutant substrate under conditions of controlled pH (e.g., around 7.0) and with addition of nutrient salts as commonly employed in the art, until, as a result of continuing increase in the substrate concentration, the evolution of carbon dioxide (and also of methane in a methanogenic process and of molecular nitrogen in a denitrification) from the digester begins to decrease while the chemical oxygen demand of the effluent begins to increase. This identifies the maximum allowable concentration of pollutant substrate. As has been explained, these techniques are widely understood such that, although experimentation is of necessity required in determining the digestion characteristics of a given waste water, the determination of the maximum allowable substrate concentration which is the first step in applying the present invention to a new pollutant species is well within the skill of the average worker in the field of biological waste treatment.

Once the maximum allowable substrate concentration is determined as explained above, it is, of course, a matter of simple mathematics to determine the minimum recycle ratio required to effect sufficient dilution of the waste water that the substrate concentration does not exceed the maximum allowable level above which action of the biomass is inhibited.

Another factor to be considered in determining the amount of recycled effluent is the pH of the liquid entering the filter. As previously explained, in an anaerobic methanogenic process, the second stage or methane forming organisms require a pH of about 6.0 to 8.0. And a process wherein denitrification is accomplished, the microorganisms require a pH generally of about 6.2 to 9.0, more usually within the range of 7.0 to 9.0 and preferably 7.0 to 8.0. The relationship of the amount of recycle to the maintenance of the desired pH in the filter is similar to that in the prior art submerged filters and will not be discussed in detail herein. Reference is made to Belgium Pat. No. 828,916 issued to Celanese Corporation on Nov. 10, 1975 for a detailed discussion of the relationship between pH and recycle in a submerged filter. The same considerations are applicable to the present invention. In some cases it may be necessary to add alkaline reagents or acid reagents to the liquid passed to the filter in order to maintain the desired pH.

The feeding and recycling to the filter are preferably both effected in continuous fashion. However, since the waste used as the fresh feed may vary considerably in strength and composition from time to time, the rate of feed of fresh waste water may be decreased, or even discontinued temporarily, and the recycle ratio increased, during operation of the process. Also, the fresh feed may be supplied regularly but intermittently, with continuous recycle.

In addition to other reagents which may be added, the filter should be supplied with nitrogen and phosphorus nutrients for the biomass. These nutrients are especially helpful in the conversion of heavy metals to insoluble sulfides. Frequently, the source of any added sulphur can also be the source of the nutrient; for example, nitrogen nutrients can be employed in the form of ammonium sulfate. The ratio of nitrogen to phosphorus should generally be roughly about 5 mg of nitrogen per mg of phosphorus. Generally in an anaerobic methanogenic process the amount of nutrients added will be to provide from about 1 to 10 mg of nitrogen and 0.1 to 5.0 mg of phosphorus per 1000 mg C.O.D, although slightly larger amounts may be required and desirable for carbohydrate-type wastes. In a denitrification process, the amount of nutrients needed will usually be greater, and will generally be so as to provide about 5 to 50 mg nitrogen and 0.7 to 7 mg phosphorus per 1000 mg C.O.D. The nitrogen may be applied in the form of, for example, urea, ammonia or an ammonium salt; and the phosphorus may be supplied in the form of phosphoric acid or as ammonium phosphate, as examples. It is also desirable to supply cobalt, preferably as the cobaltous form, generally in amounts of 0.1 mg or more, of cobalt per liter of liquid passed to the filter. Another essential trace element is iron, but iron normally exists in sufficient amounts in almost every waste water to be treated.

The pressure maintained in the filter is of relatively minor importance but is typically about atmospheric pressure because there is little need for operating under pressure or vacuum. In some instances operation under some pressure has a practical advantage if it is desired to collect the evolving gases for use as fuel, or if it is desired to pass the gas through a scrubbing tower in order to incorporate the carbon dioxide into the fresh waste water for purposes of pH adjustment. However, operation under pressure will require more expensive materials of construction of the packed tower. As pointed out above, the major advantages of the filter of the present invention is that it may be constructed of very lightweight materials. Although the temperature may vary somewhat from process to process, generally the temperature will be within the range of about 30° to 60° C. More usually the temperature will be within the range of about 35° to 40° C. Most microorganisms function best in the "mesophilic" range of 37°±2° C., although some organisms prefer a "thermophilic" range of about 50° to 55° C. The apparatus utilized for conduct of the present invention may vary widely. The preferred form of packed tower or vessel has a cylindrical portion containing the packing with an inverted cone-shaped bottom. However, the sealed vessel used in the invention may be of various shapes and may have a rectangular cross-section, or the like. There must be a void space above the packing where gases may accumulate, and there must be a lower void sump space where liquids descending from the packing may accumulate and be removed. The sump preferably has sloping sides which will direct any loose biomass to the drain or opening (line 21 of the FIGURE) provided for removal of loose biomass. The means for distributing the liquid mixture over the upper end of the packing may be of various types and may be fixed, rotating or the like as long as it distributes the liquid substantially uniformly over the cross-sectional area of the packed section.

EXAMPLES

In order to conduct a series of Experiments, a biological filter apparatus was constructed in accordance with the present invention corresponding substantially to that illustrated in the FIGURE, and all references herein to line or apparatus numbers correspond to those in the FIGURE. The tower 13 was constructed from a vertical tube having an inside diameter of 8 inches with a packed section 46 inches in depth packed with 2-inch polypropylene Pall rings. Recirculation through line 11 was by means of a centrifugal pump (not illustrated in the FIGURE) at a rate sufficient to keep the liquid level in the bottom of tower 13 below the packing, and was accomplished through use of a liquid level control device.

The sprinkler device 12 utilized for distribution of liquid over the top of the packing was, for some initial Experiments, a rotating propeller onto which the liquid impinged, but for later Experiments consisted of a spray nozzle to deliver a full cone of droplets. Samples were taken periodically of the offgas through line 16 and analyzed by mass spectrometer; and samples were also periodically taken of the outfall through line 19 and periodically sampled. Flow rates of the various inlet streams and effluent streams were also monitored.

Line 15 was used for the injection of gases in some of the below described Experiments as specifically indicated, but unless specifically indicated line 15 was not utilized and remained closed. Likewise, line 23 was not used except as specifically indicated in the Experiments.

Prior to the beginning of the Experiment I below, a biomass was formed on the Pall rings from use of domestic sludge recirculated through the packed section via line 11 concurrently with oxygen being fed through line 15. The use of oxygen was not, however, essential to the formation of a biomass; and, for a nitrogenic process, nitrous oxide or nitrogen dioxide could instead be utilized through line 15 to help form a biomass. It is not necessary that a biomass be formed in the manner indicated above, and a process to be conducted according to the present invention could, in most cases, be started without the prior formation of a biomass because the biomass would result from the conduct of the process itself.

The apparatus was operated substantially continuously after start-up, the initial period of operation having been for the formation of the biomass as discussed above, followed by a period of operation in which various experiments were conducted, including the Experiments I–IV below. No appreciable time was needed for the biomass to acclimate or adjust itself to a new feed stock, even when switching from an anaerobic methanogenic process to a non-methanogenic process and vice versa.

In the Experiments the symbol "g" represents gram, the symbol "l" represents liter, and the symbol "d" represents day. The indicated percentages of components of the offgas are by volume.

EXPERIMENT I

The first of the Experiments was conducted for a period of 27 days. The purpose of the Experiment I was to test the efficacy of the filter for denitrification of a synthetic feed stock containing, in addition to water, 7.33 grams per liter (g/l) of methanol and 15.7 g/l nitric acid. This synthetic feed stock had about 11 g/l C.O.D. from the methanol and about 10 g/l available oxygen from the nitric acid, and had a T.O.C. (total organic carbon) of 2,500 mg/l. Stoichiometries were as follows:

$$CH_3OH + 3[O] \rightarrow CO_2 + 2H_2O \qquad III$$

$$2HNO_3 \rightarrow H_2O + N_2 + 5[O] \qquad IV$$

In the following Table I, other process parameters and results for typical days of Experiment I are indicated.

TABLE I

|  | Day No. 1 | Day No. 15 | Day No. 15 |
|---|---|---|---|
| Fresh feed, l/d | 7.07 | 11.97 | 11.44 |
| Offgas, l/d | 31.5 | 63.0 | 70.7 |
| Offgas, % N$_2$ | 66.3 | 55.6 | 49.6 |
| Offgas, % N$_2$O | 0.2 | 0.0 | 0.3 |
| Offgas, % CH$_4$ | 2.5 | 1.2 | 1.4 |
| Offgas, C.O.D., g/d | 71.9 | 118.8 | 120.1 |
| C.O.D. removed in Offgas, % | 92.5 | 90.2 | 95.4 |
| Nitrogen removal, % | 99.9 | 99.9 | 99.6 |
| Outfall T.O.C., mg/l | 74 | 191 | 180 |
| T.O.C. removed in Outfall, % | 97.3 | 93.1 | 93.5 |

An interesting observation of Experiment I is that the offgas contained small, but significant, amounts of methane in spite of the prior art's claimed strong inhibition of methanogenesis by strong oxidizers.

EXPERIMENT II

Experiment II was conducted for a period of 65 days. The synthetically prepared feed stock for Experiment II was an aqueous solution of methanol containing about 7.33 g/l of methanol. In this Experiment II, nitrous oxide was fed through line 15 to ascend through the packed section, and no effort was made to keep the ratio of nitrous oxide to feed stock at a constant level; and, on many days of operation the amount of nitrous oxide was insufficient for total oxidation of the methanol substrate. Various process parameters and results for typical days of operation are indicated on Table II.

TABLE II

|  | Day No. 4 | Day No. 18 | Day No. 39 |
|---|---|---|---|
| Fresh feed, l/d | 5.90 | 8.20 | 8.88 |
| $N_2O$ feed, l/d | 34.8 | 119.7 | 121.6 |
| Nitrogen feed, g/d | 40.6 | 139.7 | 141.9 |
| Offgas, l/d | 55.2 | 151.4 | 162.8 |
| Offgas, % $N_2$ | 61.2 | 68.9 | 69.2 |
| Offgas, % $N_2O$ | 0.2 | 9.9 | 5.7 |
| Offgas, % $CH_4$ | 12.5 | 0.50 | 1.80 |
| Offgas, N content, g/d | 39.5 | 139.2 | 142.3 |
| N accountability, % | 97.4 | 99.6 | 100.3 |
| Outfall T.O.C., g/l | 0.32 | 0.21 | 0.28 |
| T.O.C. removed in outfall, % | 87.2 | 91.6 | 88.9 |
| C.O.D. removed in offgas, g/d | 40.9 | 71.6 | 82.9 |
| C.O.D. removal in offgas, % | 69.4 | 87.3 | 93.4 |

Experiment II results indicated that when nitrous oxide was used in excess it appeared in the offgas; and when C.O.D. fed was in excess of oxidizing power there was methane in the offgas. Generation of methane generally came close to compensating for insufficient nitrous oxide in regard to C.O.D. removal.

EXPERIMENT III

Experiment III was conducted for a period of 13 days. Experiment III was substantially the same as Experiment II except that the gas fed through line 15 consisted of a mixture of nitrous oxide and oxygen in the molar ratio of 9 moles nitrous oxide per one mole of oxygen. The purpose of adding the oxygen was to ascertain whether or not the oxygen would inhibit denitrification as reported in the prior art. Various process parameters and results for typical days of operation are indicated in the following Table III.

TABLE III

|  | Day No. 3 | Day No. 8 | Day No. 10 |
|---|---|---|---|
| Fresh feed, l/d | 13.69 | 13.52 | 8.41 |
| Gas fed, l/d | 96.6 | 101.7 | 102.0 |
| Nitrogen feed, g/d | 101.5 | 106.8 | 107.1 |
| Offgas, l/d | 148.8 | 149.1 | 135.3 |
| Offgas, % $N_2$ | 55.3 | 53.2 | 62.6 |
| Offgas, % $N_2O$ | 1.1 | 2.7 | 2.2 |
| Offgas, % $CH_4$ | 15.8 | 14.2 | 3.5 |
| Offgas, N content, g/d | 97.9 | 97.2 | 102.3 |
| N accountability, % | 96.5 | 91.0 | 95.5 |
| Outfall T.O.C., g/l | 0.04 | 0.03 | 0.06 |
| T.O.C. removed in outfall, % | 98.4 | 98.8 | 97.6 |
| C.O.D. removed in offgas, g/d | 130.4 | 122.9 | 82.7 |
| C.O.D. removal in offgas, % | 95.3 | 90.9 | 98.3 |

The results of Experiment III indicated that in the present process that, contrary to prior art statements, oxygen did not inhibit denitrification, and, surprisingly the presence of oxygen did not appear to adversely affect methanogenesis as indicated by the methane content of the offgas.

EXPERIMENT IV

The purpose of Experiment IV was to determine the efficacy of the filter for an anaerobic methanogensis process. The synthetically prepared feed stock was an aqueous solution of methanol which contained 2.67% by weight of methanol (40 g/l C.O.D.) on the first nine days of Experiment IV and 5.33% by weight of methanol (80 g/l C.O.D.) thereafter. This Experiment was conducted for a period of 27 days, and process parameters and results for typical days are indicated in the following Table IV.

TABLE IV

|  | Day No. 3 | Day No. 15 | Day No. 24 |
|---|---|---|---|
| Fresh feed, l/d | 13.48 | 8.79 | 8.33 |
| C.O.D. fed, g/d | 539.1 | 703.5 | 666.4 |
| Offgas, l/d | 237.6 | 264.4 | 300.7 |
| Offgas, % $CH_4$ | 71.8 | 73.5 | 74.3 |
| C.O.D. removed in offgas, g/d | 455.0 | 518.1 | 595.8 |
| C.O.D. removal in offgas, % | 84.4 | 73.7 | 89.4 |
| Outfall C.O.D., g/l | 6.32 | 13.6 | 9.92 |
| C.O.D. removed in outfall, % | 84.2 | 83.0 | 87.6 |

As may be seen from Table IV, C.O.D. removal efficiencies were good.

When Experiment IV is repeated except that hydrogen gas is passed to tower 13 through line 15 at a rate to provide about 3.2 moles of hydrogen per mole of carbon dioxide formed in the biodegradation, the hydrogen ascends through the packing and reacts with the carbon dioxide to form methane according to the reaction of Formula II discussed above. This results in much more methane being produced in the offgas, and results in a lower carbon dioxide content of the offgas.

When adding hydrogen gas to react with the carbon dioxide formed in the filter, the amount of hydrogen added should be less than the stoichiometric quantities required for complete reaction with the carbon dioxide produced, that is be less than four moles of hydrogen per mole of carbon dioxide produced in the filter. The reason for this is that it is desirable to have at least small amounts of carbon dioxide unreacted and present in the filter. If excess hydrogen is present such that all of the carbon dioxide formed in the filter is reacted, the unreacted hydrogen can interfere with the activity of the filter and have a detrimental effect. Preferably the amount of hydrogen added is not greater than 3.8 moles of hydrogen, and more preferably not greater than 3.5 moles of hydrogen, per mole of carbon dioxide formed in the filter. Usually the amount of hydrogen added will be such as to provide from 0.1 to 3.5 moles of hydrogen per mole of carbon dioxide formed in the filter.

Unlike the use of excess hydrogen, the addition of excess nitrogen oxides in a denitrification process such as Experiments II and III is not harmful. The excess and unreacted nitrogen oxides will merely appear in the offgas, but will not cause any detrimental effects to the filter. The amount of gaseous nitrogen oxides fed to the apparatus at a point below the packing should of course not be of such an amount or volume that would substantially interefere with the hydraulics of the liquid trickling downwardly through the packing or which would prevent such downward flow.

The embodiments of the invention in which an exclusive right or privilege is claimed are defined as follows:

1. A continuous biological degradation process wherein a liquid waste water stream containing organic pollutants amenable to biological degradation is contacted with a biomass of microorganisms located on the surface of a support packing so as to effect the biological degradation of said organic pollutants to carbon dioxide and other products, said microorganisms being capable of degrading said organic pollutants to carbon dioxide and other products, said process being conducted in the absence of added molecular oxygen, which process comprises:

(a) continuously passing a liquid mixture comprised of said waste water stream and the hereafter defined recycle stream downwardly through a packed section confined within a sealed vessel, said packed section being filled with the said support packing on the surface of which is a said biomass of said microorganisms, said sealed vessel being sealed whereby air and other sources of molecular oxygen cannot enter said sealed vessel, such that said liquid mixture intimately contacts said biomass as its descends through said packed section under conditions whereby at least a portion of the organic pollutants from said waste water stream are biologically degraded and converted to carbon dioxide and other products and resulting in a liquid effluent from the lower end of said packed section containing a lower concentration of said organic pollutants than in said liquid mixture, and whereby liquid descends through said packed section while carbon dioxide and other gases generated in the biological degradation ascend through said packed section countercurrently to the descending liquid, the contacting of said liquid mixture with said biomass being accomplished at a temperature within the range of about 10° to 60° C. which is suitable for said biological degradation and at substantially atmospheric pressure;

(b) continuously withdrawing from the upper end of said sealed vessel at a point above said packed section the said carbon dioxide and other gases generated in the said biological degradation;

(c) continuously withdrawing said liquid effluent from the lower end of said sealed vessel at a point below said packed section, the rate of withdrawal of said liquid effluent being such as to maintain the liquid level of any said liquid effluent accumulating in the bottom of said sealed vessel below said packed section, a portion of said liquid effluent being withdrawn as a treated waste water outfall stream; and (d) continuously recycling as a said recycle stream a portion of said liquid effluent withdrawn from the lower end of said sealed vessel and mixing said recycle stream with said waste water stream prior to passing the resulting said liquid mixture downwardly through said packed section in accordance with the preceding step (a), the portion of said liquid effluent so recycled as said recycle stream being at least 60% thereof and an amount that, when mixed with said waste water stream, will cause the said liquid mixture to have a concentration of said organic pollutants and of any biostatic or biocidal species to be below that concentration which would inhibit the growth processes of said microorganisms.

2. The process of claim 1 wherein the said liquid mixture passed downwardly through said packed section is buffered to a pH that would not inhibit the growth processes of said microorganisms and would not kill the said microorganisms.

3. The process of claim 2 wherein the weight ratio of said recycle stream to said waste water stream is within the range of about 5:1 to 100:1, and wherein the C.O.D. of the resulting said liquid mixture is within the range of about 500 to 20,000 milligrams per liter.

4. The process of claim 3 wherein the void volume of said packed section is at least about 60% of the unpacked volume of said packed section, wherein the surface area of packing in said packed section is at least 10 square feet per cubic foot, and wherein the said liquid mixture is passed to said packed section at a rate to provide a C.O.D. loading within the range of about 0.2 to 4.0 C.O.D. per cubic foot of void volume of said packed section per day, and to provide from about 0.1 to 10 volumes of said liquid mixture per void volume of said packed section per day.

5. The process of claim 4 wherein said organic pollutants are water soluble.

6. The process of claim 1 wherein said organic pollutants are water soluble.

7. The process of claim 1 wherein said waste water stream contains heavy metals toxic to said biomass, and wherein a sulfur compound is added to react with and precipitate the heavy metals as insoluble sulfides.

8. The process of claim 7 wherein said sulfur compound is gaseous hydrogen sulfide which is added in the form of a gas to said sealed vessel at a point below said packed section whereby said hydrogen sulfide ascends through said packed section countercurrently to and in intimate contact with the descending liquid.

9. A continuous methanogenic, anaerobic biological degradation process wherein denitrification is not accomplished and wherein a liquid waste water stream containing organic pollutants amenable to biological degradation is contacted with a biomass of anaerobic microorganisms located on the surface of a support packing so as to effect the biological degradation of said organic pollutants to carbon dioxide, methane and other products, said microorganisms being capable of degrading said organic pollutants to carbon dioxide, methane and other products, said process being conducted in the absence of molecular oxygen, which process comprises:

(a) continuously passing a liquid mixture comprised of said waste water stream and the hereafter defined recycle stream downwardly through a packed section confined within a sealed vessel, said packed section being filled with the said support packing on the surface of which is a said biomass of said microorganisms, said sealed vessel being sealed whereby air and other sources of molecular oxygen cannot enter said sealed vessel, such that said liquid mixture intimately contacts said biomass as it descends through said packed section under conditions whereby at least a portion of the organic pollutants from said waste water stream are biologically degraded and converted to carbon dioxide, methane, and other products and resulting in a liquid effluent from the lower end of said packed section containing a lower concentration of said organic pollutants than in said liquid mixture, and whereby liquid descends through said packed section while carbon dioxide, methane and other gases generated in the biological degradation ascend through said packed section countercurrently to the descending liquid, the contacting of said liquid mixture with said biomass being accomplished at a temperature within the range of about 10° to 60° C. which is suitable for said biological degradation and at substantially atmospheric pressure;

(b) continuously withdrawing from the upper end of said sealed vessel at a point above said packed section the said carbon dioxide, methane and other gases generated in the said biological degradation;

(c) continuously withdrawing said liquid effluent from the lower end of said sealed vessel at a point below said packed section, the rate of withdrawal of said liquid effluent being such as to maintain the liquid level of any said liquid effluent accumulating in the bottom of said sealed vessel below said packed section, a portion of said liquid effluent being withdrawn as a treated waste water outfall stream; and (d) continuously recycling as a said recycle stream a portion of said liquid effluent withdrawn from the lower end of said sealed vessel and mixing said recycle stream with said waste water stream prior to passing the resulting said liquid mixture downwardly through said packed section in accordance with the preceding step (a), the portion of said liquid effluent so recycled as said recycle stream being at least 60% thereof and an amount that, when mixed with said waste water stream, will cause the said liquid mixture to have a concentration of said organic pollutants and of any biostatic or biocidal species to be below that concentration which would inhibit the growth processes of said microorganisms.

10. The process of claim 9 wherein the said liquid mixture passed downwardly through said packed section is buffered to a pH that would not inhibit the growth processes of said microorganisms and would not kill the said microorganisms.

11. The process of claim 10 wherein the weight ratio of said recycle stream to said waste water stream is within the range of about 5:1 to 100:1, and wherein the C.O.D. of the resulting said liquid mixture is within the range of about 500 to 20,000 milligrams per liter.

12. The process of claim 11 wherein the void volume of said packed section is at least about 60% of the unpacked volume of said packed section, wherein the surface area of packing in said packed section is at least 10 square feet per cubic foot, and wherein the said liquid mixture is passed to said packed section at a rate to provide a C.O.D. loading within the range of about 0.2 to 4.0 C.O.D. per cubic foot of void volume of said packed section per day, and to provide from about 0.1 to 10 volumes of said liquid mixture per void volume of said packed section per day.

13. The process of claim 12 wherein said organic pollutants are water soluble.

14. The process of claim 12 wherein a gas comprising hydrogen is passed to said sealed vessel at a point below said packed section whereby said hydrogen ascends through said packed section countercurrently to and in intimate contact with the descending liquid, the amount of said gas being passed to said sealed vessel being such as to provide not greater than about 3.5 moles of hydrogen per mole of carbon dioxide being formed in said biological degradation.

15. The process of claim 14 wherein said organic pollutants are water soluble.

16. The process of claim 9 wherein said organic pollutants are water soluble.

17. The process of claim 9 wherein said waste water stream contains heavy metals toxic to said biomass, and wherein a sulfur compound is added to react with and precipitate the heavy metals as insoluble sulfides.

18. The process of claim 17 wherein said sulfur compound is gaseous hydrogen sulfide which is added in the form of a gas to said sealed vessel at a point below said packed section whereby said hydrogen sulfide ascends through said packed section countercurrently to and in intimate contact with the descending liquid.

19. The process of claim 9 wherein a gas comprising hydrogen is passed to said sealed vessel at a point below said packed section whereby said hydrogen ascends through said packed section countercurrently to and in intimate contact with the descending liquid, the amount of said gas being passed to said sealed vessel being such as to provide not greater than about 3.8 moles of hydrogen per mole of carbon dioxide being formed in said biological degradation.

20. A continuous biological degradation process wherein a liquid waste water stream containing organic pollutants amenable to biological degradation, and also containing nitrogen compounds wherein combined nitrogen is present as a nitrate, a nitrite or a nitrogen oxide, is contacted with a biomass of microorganisms located on the surface of a support packing so as to effect the biological degradation or conversion of said organic pollutants to carbon dioxide and other products, and to effect the biological degradation or conversion of said combined nitrogen to molecular nitrogen, said microorganisms being capable of degrading said organic pollutants to carbon dioxide and other products and of degrading or converting said combined nitrogen to molecular nitrogen, said process being conducted in the absence of added molecular oxygen, which process comprises:

(a) continuously passing a liquid mixture comprised of said waste water stream and the hereafter defined recycle stream downwardly through a packed section confined within a sealed vessel, said packed section being filled with the said support packing on the surface of which is a said biomass of said microorganisms, said sealed vessel being sealed whereby air and other sources of molecular oxygen cannot enter said sealed vessel, such that said liquid mixture intimately contacts said biomass as it descends through said packed section under conditions whereby at least a portion of the organic pollutants from said waste water stream are biologically degraded and converted to carbon dioxide and other products and at least a portion of the combined nitrogen from said waste water stream is converted to molecular nitrogen and resulting in a liquid effluent from the lower end of said packed section containing a lower concentration of said organic pollutants and a lower concentration of said nitrogen compounds than in said liquid mixture, and whereby liquid descends through said packed section while carbon dioxide, molecular nitrogen and other gases generated in the biological degradation ascend through said packed section countercurrently to the descending liquid, the contacting of said liquid mixture with said biomass being accomplished at a temperature within the range of about 10° to 60° C. which is suitable for said biological degradation and at substantially atmospheric pressure;

(b) continuously withdrawing from the upper end of said sealed vessel at a point above said packed section the said carbon dioxide, molecular nitrogen and other gases generated in the said biological degradation;

(c) continuously withdrawing said liquid effluent from the lower end of said sealed vessel at a point below said packed section, the rate of withdrawal of said liquid effluent being such as to maintain the liquid level of any said liquid effluent accumulating in the bottom of said sealed vessel below said packed section, a portion of said liquid effluent being withdrawn as a treated waste water outfall stream; and (d) continuously recycling as a said recycle stream a portion of said liquid effluent withdrawn from the lower end of said sealed vessel and mixing said recycle stream with said waste water stream prior to passing the resulting said liquid mixture downwardly through said packed section in accordance with the preceding step (a), the portion of said liquid effluent so recycled as said recycle stream being at least 60% thereof and an amount that, when mixed with said waste water stream, will cause the said liquid mixture to have a concentration of said organic pollutants, and of any said nitrogen compounds, and of any biostatic or biocidal species to be below that concentration which would inhibit the growth processes of said microorganisms.

21. The process of claim 20 wherein the said liquid mixture passed downwardly through said packed section is buffered to a pH that would not inhibit the growth processes of said microorganisms and would not kill the said microorganisms.

22. The process of claim 21 wherein the weight ratio of said recycle stream to said waste water stream is within the range of about 5:1 to 100:1, and wherein the C.O.D. of the resulting said liquid mixture is within the range of about 500 to 20,000 milligrams per liter.

23. The process of claim 22 wherein the void volume of said packed section is at least about 60% of the unpacked volume of said packed section, wherein the surface area of packing in said packed section is at least 10 square feet per cubic foot, and wherein the said liquid mixture is passed to said packed section at a rate to provide a C.O.D. loading within the range of about 0.2 to 4.0 C.O.D. per cubic foot of void volume of said packed section per day, and to provide from about 0.1 to 10 volumes of said liquid mixture per void volume of said packed section per day.

24. The process of claim 23 wherein said organic pollutants are water soluble.

25. The process of claim 23 wherein a gas comprising one or more nitrogen oxides is passed to said sealed vessel at a point below said packed section whereby said nitrogen oxides ascend through said packed section countercurrently to and in intimate contact with the said descending liquid.

26. The process of claim 23 wherein said organic pollutants are water soluble.

27. The process of claim 20 wherein said organic pollutants are water soluble.

28. The process of claim 20 wherein said waste water stream contains heavy metals toxic to said biomass, and wherein a sulfur compound is added to react with and precipitate the heavy metals as insoluble sulfides.

29. The process of claim 28 wherein said sulfur compound is gaseous hydrogen sulfide which is added in the form of a gas to said sealed vessel at a point below said packed section whereby said hydrogen sulfide ascends through said packed section countercurrently to and in intimate contact with the descending liquid.

30. The process of claim 20 wherein a gas comprising one or more nitrogen oxides is passed to said sealed vessel at a point below said packed section whereby said nitrogen oxides ascend through said packed section countercurrently to and in intimate contact with the said descending liquid.

31. The process of claim 30 wherein said gas comprises nitrous oxide.

* * * * *